(12) United States Patent
Arita et al.

(10) Patent No.: US 12,023,230 B2
(45) Date of Patent: Jul. 2, 2024

(54) ABSORBENT ARTICLE

(71) Applicant: KAO CORPORATION, Tokyo (JP)

(72) Inventors: Kosuke Arita, Utsunomiya (JP); Yuko Fukuda, Mashiko-machi (JP); Yasuyuki Okuda, Utsunomiya (JP); Akiyuki Ueda, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 1063 days.

(21) Appl. No.: 16/770,199

(22) PCT Filed: Dec. 27, 2017

(86) PCT No.: PCT/JP2017/047069
§ 371 (c)(1),
(2) Date: Jun. 5, 2020

(87) PCT Pub. No.: WO2019/130509
PCT Pub. Date: Jul. 4, 2019

(65) Prior Publication Data
US 2020/0289340 A1    Sep. 17, 2020

(51) Int. Cl.
*A61F 13/15* (2006.01)
*A61F 13/49* (2006.01)

(52) U.S. Cl.
CPC .. *A61F 13/49011* (2013.01); *A61F 13/49001* (2013.01); *A61F 2013/49028* (2013.01); *A61F 2013/49092* (2013.01)

(58) Field of Classification Search
CPC .......... A61F 13/49011; A61F 13/49001; A61F 203/49028; A61F 203/49092
See application file for complete search history.

(56) References Cited

U.S. PATENT DOCUMENTS 4,246,900 A  *  1/1981  Schroder ........... A61F 13/49009
                                              604/389
6,156,023 A     12/2000 Yoshioka
(Continued)

FOREIGN PATENT DOCUMENTS

CN    1360489 A    7/2002
CN    1371266 A    9/2002
(Continued)

OTHER PUBLICATIONS

International Search Report, issued in PCT/JP2017/047069, PCT/ISA/210, dated Feb. 6, 2018.
(Continued)

*Primary Examiner* — Jacqueline F Stephens
(74) *Attorney, Agent, or Firm* — Birch, Stewart, Kolasch & Birch, LLP

(57) ABSTRACT

A leak-proof cuff (28) is divided into a lower region (40) and a upper region (41). The upper region (41) includes a first region (41A) located at the side of a free edge (28B) relative to the center in the width direction (Y) and a second region (41B) located at the side of a folding line (42). In each of the first region (41A) and the second region (41B), at least one elastic member (29) extending along the longitudinal direction (X) is provided in a stretched state. In a case where the elongation of the upper region (41) in a natural state is 0, and the elongation in a maximum stretched state is 100, the stress σ1 of the first region (41A) is larger than the stress σ2 of the second region (41B) at an elongation of 5, and the stress σ2 of the second region (41B) is larger than the stress σ1 of the first region (41A) at an elongation of 100.

20 Claims, 8 Drawing Sheets

(56) References Cited

U.S. PATENT DOCUMENTS

| | | |
|---|---|---|
| 6,624,340 B2 * | 9/2003 | Mizutani ............. A61F 13/4753 |
| | | 604/385.03 |
| 7,163,530 B1 | 1/2007 | Toyoshima et al. |
| 7,879,017 B1 | 2/2011 | Tabata et al. |
| 8,939,957 B2 * | 1/2015 | Raycheck ............. A61F 13/496 |
| | | 604/385.27 |
| 2004/0260262 A1 | 12/2004 | Nishitani et al. |
| 2006/0173435 A1 | 8/2006 | Nakajima et al. |
| 2016/0113823 A1 * | 4/2016 | Iwasaki ............... A61F 13/4758 |
| | | 604/385.26 |
| 2019/0262194 A1 | 8/2019 | Mukai et al. |

FOREIGN PATENT DOCUMENTS

| | | | | |
|---|---|---|---|---|
| EP | 1 219 274 A1 | 7/2002 | | |
| EP | 1219274 A1 * | 7/2002 | ....... | A61F 13/49017 |
| JP | 11-276520 A | 10/1999 | | |
| JP | 2000-262555 A | 9/2000 | | |
| JP | 2001-25485 A | 1/2001 | | |
| JP | 2004-290498 A | 10/2004 | | |
| JP | 2005-7076 A | 1/2005 | | |
| JP | 2014-230571 A | 12/2014 | | |
| RU | 2 389 458 C2 | 5/2010 | | |
| WO | WO 2017/213096 A1 | 12/2017 | | |

OTHER PUBLICATIONS

Extended European Search Report for European Application No. 17936002.9, dated Jul. 16, 2021.

* cited by examiner

ABSORBENT ARTICLE

TECHNICAL FIELD

The present invention relates to an absorbent article having leak-proof cuffs.

BACKGROUND ART

Absorbent articles such as a disposable diaper and a sanitary napkin may have leak-proof cuffs extending along the longitudinal direction in both side regions in the width direction in order to improve contact around the legs of a wearer wearing the article and to prevent liquid leakage from the article. For example, Patent Literature 1 discloses that leak-proof cuffs extending along the front-to-rear direction on the inner face of a disposable diaper each have a protrusion capable of rising from the inner face of the diaper and a sealing face region including a first overhanging portion inward from the protrusion and a second overhang portion outward from the protrusion. A first elastic member of the first overhanging portion located in the inside edge portion of the sealing face region has a higher elongation stress than that of a second elastic member of the second overhanging portion located in the outside edge portion of the sealing face region.

Patent Literature 2 discloses a disposable absorbent article having rising cuffs, and each rising cuff in a stretched state in the longitudinal direction includes a rising portion rising from the rising edge thereof toward the center of the article and a flat contact portion folded midway of the cuff and inverted outward. In each of the flat contact portion and the rising portion, a plurality of elastic members are provided at intervals in the width direction.

Patent Literature 3 discloses an absorbent article having leak-proof cuffs with elastic members, and by shifting the plurality of elastic members bonded to the leak-proof cuff and/or by varying the contraction force of the elastic members, grooves or creases due to the contraction force of the elastic members are formed in a direction intersecting the width direction of the absorbent article.

CITATION LIST

Patent Literatures

Patent Literature 1: JP 11-276520 A
Patent Literature 2: JP 2001-25485 A
Patent Literature 3: JP 2004-290498 A

SUMMARY OF INVENTION

The present invention relates to an absorbent article including leak-proof cuffs extending along a longitudinal direction and located at side regions in a width direction of the absorbent article.

The leak-proof cuff is folded on a folding line extending along the longitudinal direction of the leak-proof cuff and is divided into an upper region and a lower region at the folding line.

In the leak-proof cuff folded on the folding line, the folding line is located inside in the width direction from a free edge of the leak-proof cuff.

The upper region includes a first region located at a side of the free edge relative to a center of the upper region in the width direction and a second region located at a side of the folding line.

In each of the first region and the second region, at least one elastic member extending along the longitudinal direction is provided in a stretched state.

In a case where an elongation of the upper region in a natural state is defined as 0, and an elongation in a maximum stretched state is defined as 100.

A stress $\sigma 1$ of the first region is larger than a stress $\sigma 2$ of the second region at an elongation of 5.

The stress $\sigma 2$ of the second region is larger than the stress $\sigma 1$ of the first region at an elongation of 100.

DESCRIPTION OF EMBODIMENTS

An absorbent article having leak-proof cuffs easily comes in closer contact with the legs of a wearer. However, when the posture of a wearer changes, and accordingly the distance between an absorbent article and the legs of the wearer changes, the contact condition of leak-proof cuffs with the legs of the wearer is changed, and the close contact degree of the absorbent article with the legs of the wearer may deteriorate to form a clearance therebetween. Such a clearance may cause liquid leakage.

The present invention relates to an improvement of an absorbent article having leak-proof cuffs and more specifically relates to an absorbent article achieving higher contact degree between leak-proof cuffs and the legs of a wearer.

Figure 1:
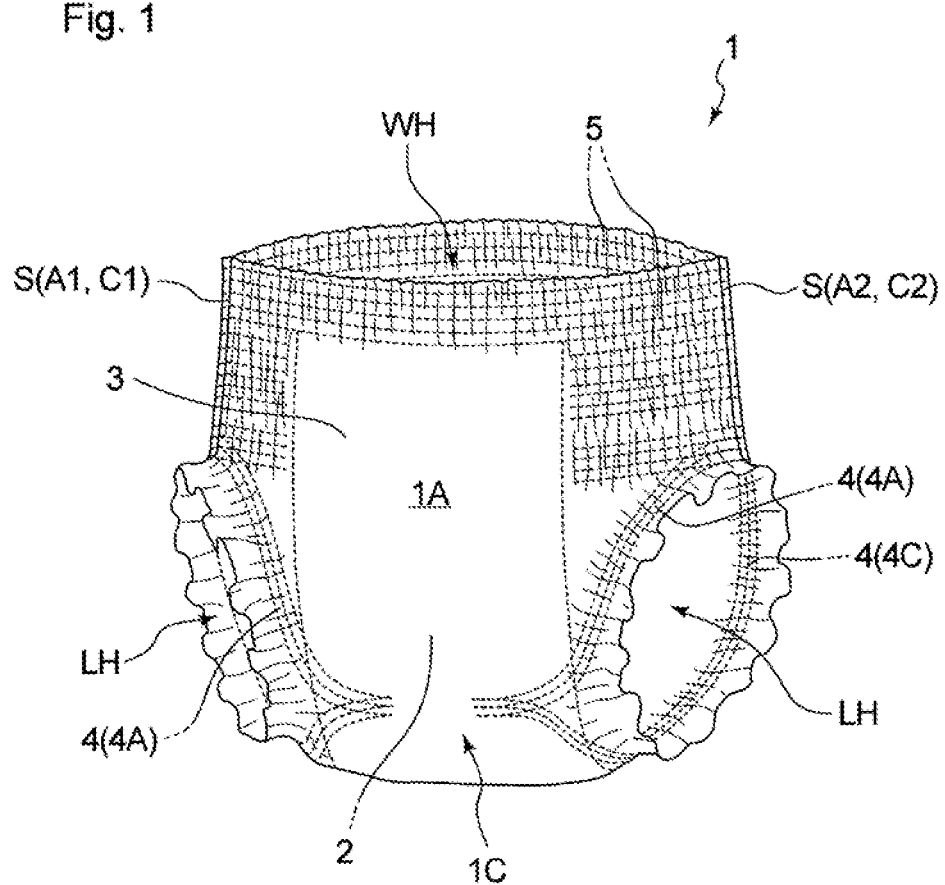
FIG. 1 is a perspective view schematically showing a pull-on disposable diaper as an embodiment of an absorbent article of the present invention.
Figure 2:
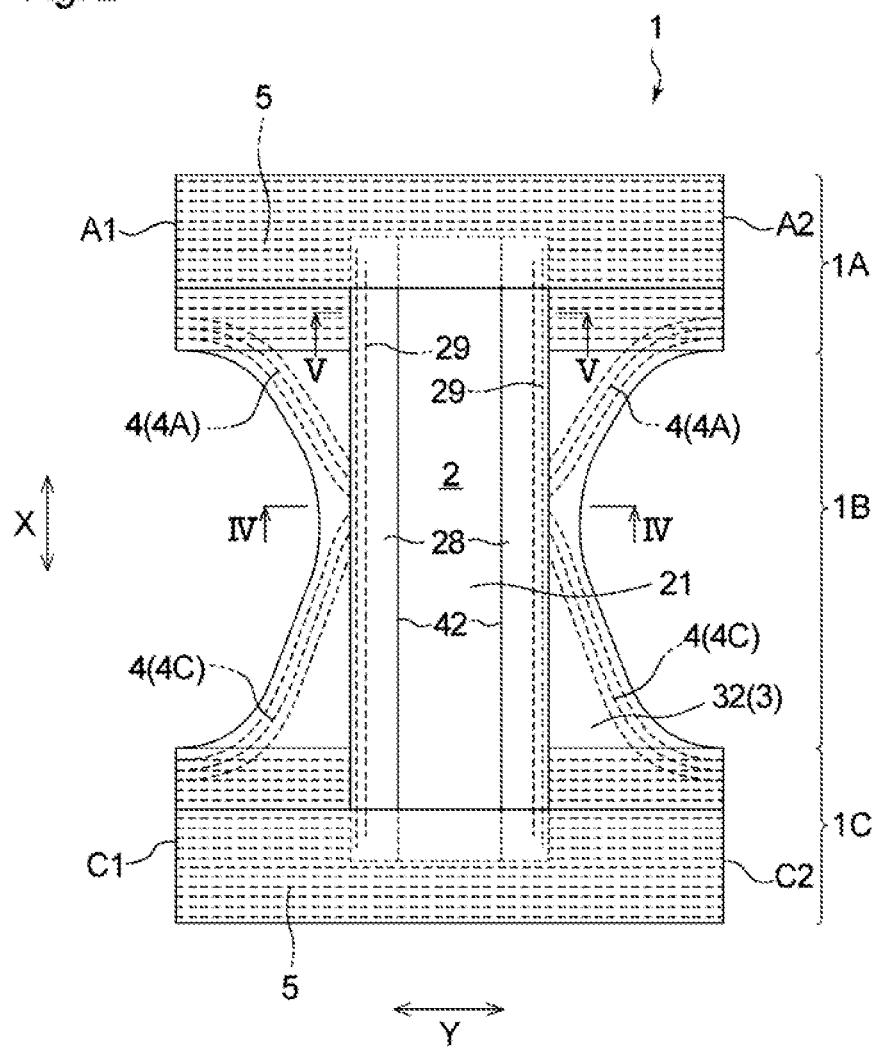
FIG. 2 is a developed plan view schematically showing a skin-facing surface side of the diaper shown in FIG. 1 in its flat-out, uncontracted state.
Figure 3:
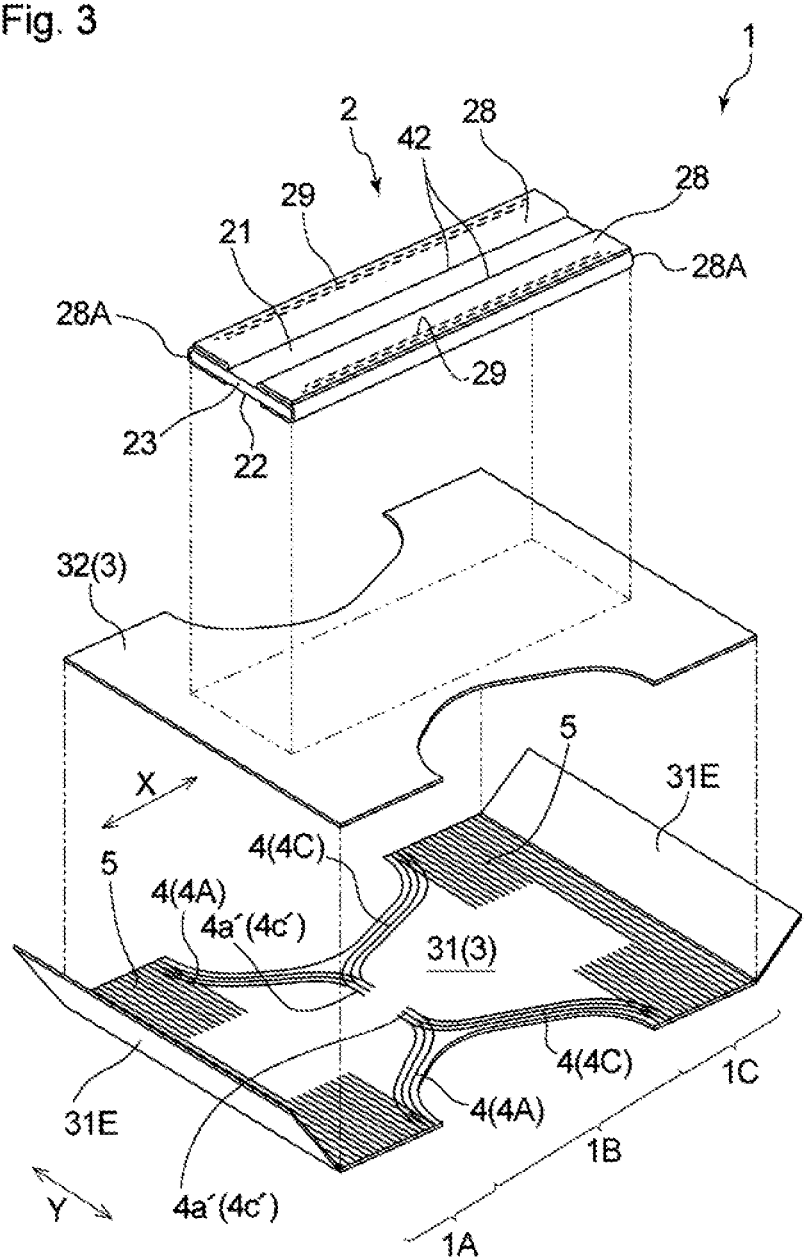
FIG. 3 is an exploded perspective view schematically showing the diaper in FIG. 1, where the diaper is disjoined.

The present invention will now be described on the basis of preferred embodiments thereof with reference to drawings. FIG. 1 to FIG. 3 show schematic configurations of a pull-on disposable diaper 1 as an embodiment of the absorbent article of the present invention. The diaper 1 includes a front portion 1A to be placed on the front side of a wearer, a rear portion 1C to be placed on the rear side, and a crotch portion 1B located therebetween. The diaper 1 has a longitudinal direction X extending from the front portion 1A across the crotch portion 1B to the rear portion 1C and a width direction Y orthogonal thereto.

The diaper 1 includes an absorbent assembly 2 having an absorbent member 23, a topsheet 21 provided on a skin-facing surface side of the absorbent member 23, and a backsheet 22 provided on a non-skin-facing surface side of the absorbent member 23 and includes an outer cover 3 located above a non-skin-facing surface side of the absorbent assembly 2 and fixing the absorbent assembly 2. In the diaper 1, the outer cover 3 in the front portion 1A and the outer cover 3 in the rear portion 1C are joined together in both lateral side edge portions along the longitudinal direction X to form a pair of side seals S and S, a waist opening WH through which the trunk of a wearer passes, and a pair of leg openings LH and LH through which the legs of a wearer pass.

In the present description, a "skin-facing surface" is one face of a diaper 1 or a constituent member thereof (for example, a topsheet) and faces the skin of a wearer at the time of wearing the diaper 1 or is the face relatively close to the skin of a wearer, and a "non-skin-facing surface" is the other face of a diaper 1 or a constituent member thereof and is a face opposite to the skin of a wearer at the time of wearing the diaper 1 (the side on clothes) or is a face relatively distant from the skin of a wearer. In the present description, "at the time of wearing" means a condition in which a typical, appropriate wearing position or a normal wearing position of the disposable diaper 1 is maintained, and excludes the case in which a diaper 1 is shifted from the wearing position.

Each of the front portion 1A and the rear portion 1C is located at the same position as the side seal S in the longitudinal direction X, and is a below-waist portion which is to be placed above the below-waist of a wearer at the time of wearing the diaper 1. The crotch portion 1B is a region having curves for forming leg openings LH and LH in both lateral side edge portions in the longitudinal direction X of the outer cover 3. The crotch portion 1B includes an excretory-facing region to face the excretory of a wearer at the time of wearing the diaper 1, and the excretory-facing region is typically located at or near the center of the diaper 1 in the longitudinal direction X.

The absorbent assembly 2 has a rectangular shape in a planar view as indicated by a profile line in FIG. 2. The absorbent assembly 2 is fixed to the center of the outer cover 3 in the width direction Y while the longitudinal direction thereof is coincident with the longitudinal direction X of the diaper 1 in its flat-out, uncontracted state. The outer cover 3, as shown in FIG. 2, forms the outer shape of the diaper 1 in a stretched state of the diaper 1, and the periphery of the outer cover 3 defines the profile line of the diaper 1 in the stretched state. The "stretched state" of a diaper 1 means a state in which side seals S are cut to flatten out the diaper 1, and each elastic member of the diaper 1 in its flat-out state is stretched to design dimensions, that is, dimensions when the diaper is flattened out into a plane while the effects of elastic members are completely eliminated.

The absorbent assembly 2 includes a liquid permeable topsheet 21 constituting a skin-facing surface, a liquid impermeable, sparingly liquid permeable, or water repellent backsheet 22 constituting a non-skin-facing surface, and a liquid-retentive absorbent member 23 interposed between the sheets 21 and 22, and is formed by integrating these members with a known joining means such as an adhesive. The absorbent member 23 is located at the center of the diaper 1 in the width direction Y. As each of the topsheet 21 and the backsheet 22, various materials conventionally used in such absorbent articles can be used without any limitation. For example, as the topsheet 21, various nonwoven fabrics and porous films can be used. As the backsheet 22, resin films, laminates of, for example, a resin film and a nonwoven fabric, and the like can be used.

As shown in FIG. 3, the absorbent member 23 has a substantially rectangular shape extending along the longitudinal direction X in a plan view and extends from the front portion 1A to the rear portion 1C. The absorbent member 23 includes a liquid-retentive absorbent core (not shown) containing an absorbent material and a core-wrap sheet (not shown) overlying the skin-facing surface and the non-skin-facing surface of the absorbent core. The absorbent core and the core-wrap sheet are joined with a known joining means such as a hot melt adhesive.

The absorbent core includes a fiber stacked core forming material containing an absorbent material. As the absorbent material, materials commonly used as the forming material of such absorbent cores can be used without any limitation. Examples of the forming material of the absorbent core include wood pulp, hydrophilic fibers such as synthetic fibers treated with a hydrophilizing agent, and water absorbing polymer particles. The absorbent core can be a fiber stacking product of hydrophilic fibers or an absorbent core in which water-absorbing polymer particles are supported on the fiber stacking product. As the core-wrap sheet, a water-permeable sheet material can be used, and paper and nonwoven fabric can be used, for example. The absorbent core can have a single layer structure or a multilayer structure depending on specific applications of the diaper 1.

Figure 4:
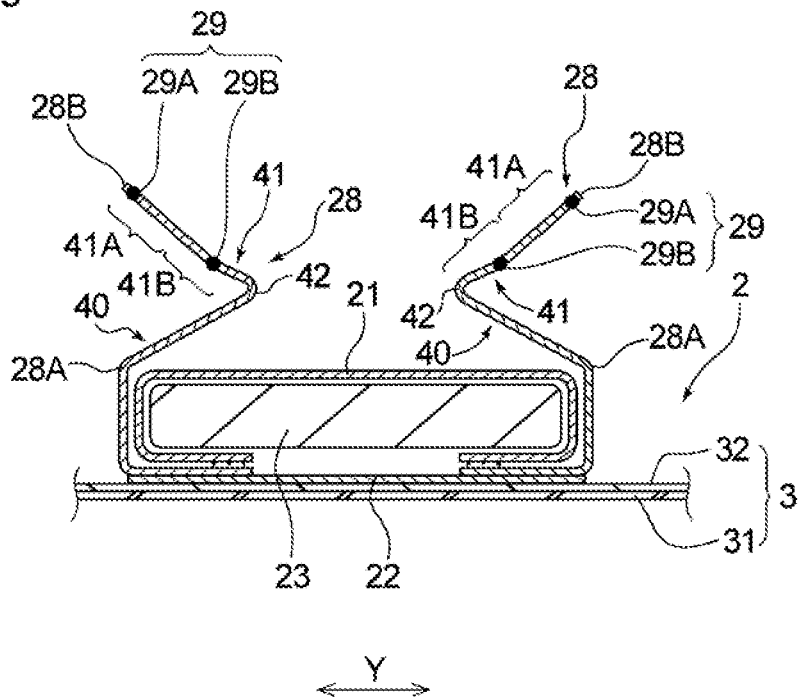
FIG. 4 is a sectional view taken along line IV-IV in FIG. 2.

As shown in FIG. 2 and FIG. 3, the diaper 1 includes a pair of leak-proof cuffs 28 and 28 extending along the longitudinal direction X in both side regions in the width direction Y on the skin-facing surface of the absorbent assembly 2. Each leak-proof cuff 28 is made from a liquid resistant or water repellent and breathable sheet material, for example. As shown in FIG. 4, the leak-proof cuff 28 has a base end section 28A and a free edge 28B each extending along the longitudinal direction X. As shown in FIG. 2 and FIG. 3, on the leak-proof cuff 28, two or more filamentous leak-proof cuff-forming elastic members 29 are provided in a stretched state. The leak-proof cuff 28 rises at least in the crotch portion 1B by contraction of the elastic members 29 provided in a stretched state at the time of wearing the diaper 1, and this prevents an excreted fluid such as urine from flowing outward in the width direction Y. The leak-proof cuff 28 will be specifically described later.

As shown in FIG. 2, the outer cover 3 is provided over the front portion 1A as the below-waist portion of the front body portion, the rear portion 1C as the below-waist portion of the back body portion, and the crotch portion 1B interposed between the front portion 1A and the rear portion 1C. In the outer cover 3, both lateral side edges along the longitudinal direction X in the crotch portion 1B are curved inward into an arc shape to form a pair of leg edge portions. As shown in FIG. 2, the outer cover 3 is constricted inward in the width direction Y in the center region in the longitudinal direction X to form a sandglass-like shape in a plan view. In the outer cover 3, both lateral side edge portions A1 and A2 along the longitudinal direction X of the front portion 1A and both lateral side edge portions C1 and C2 along the longitudinal direction X of the rear portion 1C are joined together by a known joining means such as an adhesive, heat sealing, and ultrasonic sealing, and the joining forms a pair of side seals S and S of the diaper 1 and also forms a waist opening WH and a pair of leg openings LH and LH, as shown in FIG. 1. As shown in FIG. 2 and FIG. 3, in the outer cover 3, leg elastic members 4 for forming leg gathers are provided in a stretched state in regions constituting opening edge portions of the leg openings LH. The leg elastic members 4 are filamentous or continuous members and are interposed between and fixed to an outer sheet 31 and an inner sheet 32 of the outer cover 3 with an adhesive.

As shown in FIG. 2 and FIG. 3, the leg elastic members 4 include front portion leg elastic members 4A provided along the leg openings located close to the front portion 1A and rear portion leg elastic members 4C provided along the leg openings located close to the rear portion 1C. One end of each of the front portion leg elastic members 4A and the rear portion leg elastic members 4C terminates at the corresponding side edge of the front portion 1A or the rear portion 1C. In addition, the other end regions 4a' and 4c' including the other ends of the front portion leg elastic members 4A and the rear portion leg elastic members 4C extend inward in the width direction Y in the crotch portion 1B, as shown in FIG. 3.

The outer cover 3, as shown in FIG. 3, includes the outer sheet 31 located relatively distant from the absorbent assembly 2 and the inner sheet 32 located relatively close to the absorbent assembly 2. When the diaper 1 is worn, the inner sheet 32 is located close to the body of a wearer and forms an inner face as the skin-facing surface of the diaper 1, and the outer sheet 31 is located distant from the body of a wearer and forms an outer face as the non-skin-facing surface of the diaper 1. The outer sheet 31 and the inner sheet 32 are joined together at certain positions by a known joining means such as an adhesive.

As shown in FIG. 3, the outer sheet 31 includes, in addition to a portion having the same shape and the same size as the inner sheet 32, a front extension portion 31E extending outward in the longitudinal direction X from the edge of the front portion 1A of the inner sheet 32 when the sheets 31 and 32 are laminated and a rear extension portion 31E extending outward in the longitudinal direction X from the edge of the rear portion 1C of the inner sheet 32. The extension portions 31E and 31E of the outer sheet 31 are folded toward the inner sheet 32 so as to cover the corresponding ends in the longitudinal direction X of the absorbent assembly 2 placed and fixed onto the inner sheet 32, as shown in FIG. 2, and are fixed to other constituent members (the inner sheet 32, the absorbent assembly 2, and the leak-proof cuffs 28) of the diaper 1 facing the extension portions 31E and 31E, with an adhesive. The extension portions 31E of the outer sheet 31 function as a hydrophobic sheet.

The outer cover 3 has an elasticized portion having elasticity in the width direction Y in at least one of the front portion 1A and the rear portion 1C. In the description, an "elasticized portion of an outer cover" is a portion having elasticity in the width direction Y in the outer cover 3, and in the present embodiment, portions located in the front portion 1A and the rear portion 1C of the outer cover 3 are elasticized portions. More specifically, in the present embodiment, the outer sheet 31 and the inner sheet 32 included in the outer cover 3 are non-elastic sheets having no elasticity, but between the sheets 31 and 32 in each of the front portion 1A and the rear portion 1C, a plurality of below-waist elastic members 5 are provided in a stretched state in the width direction Y. Due to the elasticity in the width direction Y of the plurality of below-waist elastic members 5, a "portion located in the front portion 1A of the outer cover 3" and a "portion located in rear portion 1C of the outer cover 3" each have elasticity in the width direction Y over the whole region thereof to be the "elasticized portion".

As shown in FIG. 4, the leak-proof cuff 28 is folded on a folding line 42 extending along the longitudinal direction of the leak-proof cuff 28, between the base end section 28A and the free edge 28B to be divided into a lower region 40 located at the side of the base end section 28A and an upper region 41 located at the side of the free edge 28B. In at least the crotch portion 1B of the diaper 1 in a natural state, the leak-proof cuff 28 is folded on the folding line 42, and the folding line 42 is located inside in the width direction Y from the free edge 28B of the leak-proof cuff 28. Accordingly, the leak-proof cuff 28 bends along the folding line 42. The lower region 40 and the upper region 41 extend in the longitudinal direction X and each have a substantially rectangular shape in a planar view. The lower region 40 and the upper region 41 partly constitute a single sheet constituting the leak-proof cuff 28. In the present description, a natural state is a relaxed state without any external force on a diaper 1 and is more particularly a state when the upper region 41 in the leak-proof cuff 28 has an elongation of 0. The elongation will be described later.

As shown in FIG. 2 and FIG. 3, the folding line 42 between the lower region 40 and the upper region 41 linearly extends in the longitudinal direction X. In both a stretched state and a natural state of the diaper 1, the folding line 42 is preferably located above the topsheet 21 from the viewpoint of preventing a body fluid of a wearer on the topsheet from coming into contact with the skin of the wearer and of reducing burden on the skin of the wearer. In both a stretched state and a natural state of the diaper 1, the folding line 42 is preferably located above the absorbent member 23 from the viewpoint of preventing leakage of a body liquid because the leak-proof cuffs 28 widely cover the skin-facing side of the absorbent member 23.

Figure 5:
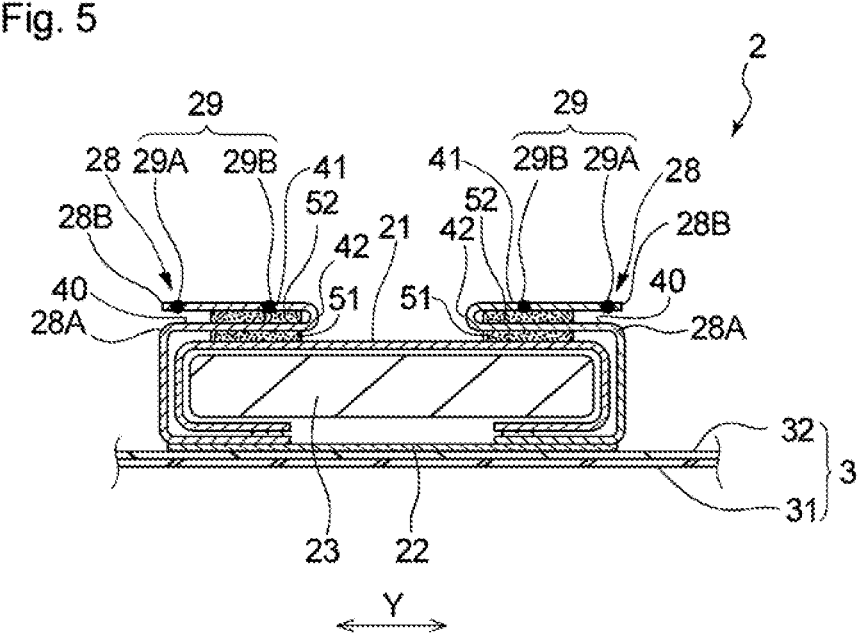
FIG. 5 is a sectional view taken along line V-V in FIG. 2.

As shown in FIG. 5, in an end region of the diaper 1 in the longitudinal direction X, the inner face of the lower region 40 of the leak-proof cuff 28 is joined to the topsheet 21 to form a first joined region 51. The first joined region 51 is formed by bonding the inner face of the lower region 40 and the skin-facing surface of the topsheet 21, for example, with an adhesive. As shown in FIG. 5, in an end region of the diaper 1 in the longitudinal direction X, the respective outer faces of the lower region 40 and the upper region 41 of the leak-proof cuff 28 are joined to form a second joined region 52. The second joined region 52 is formed as follows: a sheet constituting the leak-proof cuff 28 is folded in half along the folding line 42 while the folding line faces outward and is divided into the lower region 40 and the upper region 41; and the lower region 40 and the upper region 41 facing together are bonded, for example, with an adhesive.

The first joined regions 51 and the second joined regions 52 are formed only in the front and rear end regions of the absorbent assembly 2 in the longitudinal direction X and are not formed in a region that includes at least the crotch portion 1B and that is located between the end regions.

In the embodiment shown in FIG. 4 and FIG. 5, the free edge 28B of the leak-proof cuff 28 is located outside the side edges of the absorbent member 23 and the absorbent core (not shown) in the width direction Y. Alternatively, in at least one state of the natural state and the stretched state of the diaper 1, the free edge 28B may be located above the side edge of the absorbent member 23 or may be located inside the side edge of the absorbent member 23 in the width direction Y. With such a structure, the upper regions 41 of the leak-proof cuffs 28 cover the whole absorbent member 23.

As described above, in the leak-proof cuff 28, filamentous leak-proof cuff-forming elastic members 29 are provided, and the leak-proof cuff-forming elastic members 29 are provided in the upper region 41 of the leak-proof cuff 28 as shown in FIG. 4 and FIG. 5. The leak-proof cuff-forming elastic members 29 extend in the longitudinal direction X of the diaper 1 and are fixed in a stretched state to the upper region 41. To fix the leak-proof cuff-forming elastic members 29 to the upper region 41, for example, a sheet to constitute the leak-proof cuff 28 can be folded in half, and between the folded sheets, leak-proof cuff-forming elastic members 29 can be interposed in a stretched state and be fixed thereto with an adhesive or the like. Alternatively, a single sheet to constitute the leak-proof cuff 28 is not folded in half, but on one face of the sheet, leak-proof cuff-forming elastic members 29 can be provided in a stretched state and be fixed thereto with an adhesive or the like.

As shown in FIG. 4, the upper region 41 of the leak-proof cuff 28 has a first region 41A located at the side of the free edge 28B relative to the center of the upper region 41 in the width direction Y and a second region 41B located at the side of the folding line 42. The first region 41A and the second region 41B each have a rectangular shape extending along the longitudinal direction X in a planar view. In each of the first region 41A and the second region 41B, at least one leak-proof cuff-forming elastic member 29 extending along the longitudinal direction X is provided in a stretched state. Accordingly, two or more leak-proof cuff-forming elastic members 29 are provided in the whole upper region 41. FIG. 4 and FIG. 5 show the state in which two leak-proof cuff-forming elastic members 29 are provided in total. Not shown in the drawings, for a leak-proof cuff 28 having an elastic member on the folding line 42, the elastic member is counted as the number of elastic members provided in the second region 41B. As for the lower region 40 of the leak-proof cuff 28, elastic members may not be provided or may be provided in the lower region 40. From the viewpoint of certainly achieving the advantageous effects of the present invention described later, no elastic member is preferably provided in the lower region 40. Even when elastic members are provided in the lower region 40, the number of the elastic members is excluded from the above number of the elastic members.

As shown in FIG. 4 and FIG. 5, in the upper region 41 of the leak-proof cuff 28, a first elastic member 29A as the leak-proof cuff-forming elastic member 29 located in the first region 41A and a second elastic member 29B as the leak-proof cuff-forming elastic member 29 located in the second region 41B are provided. The first elastic member 29A is located at or near the free edge 28B. The second elastic member 29B is located at substantially the center of the second region 41B in the width direction Y. The first elastic member 29A and the second elastic member 29B are provided apart from each other. The second elastic member 29B may not be located at substantially the center of the second region 41B in the width direction Y. For example, the second elastic member 29B can be located at any position from the folding line 42 of the leak-proof cuff 28 to the vicinity of the boundary between the second region 41B and the first region 41A.

The first region 41A and the second region 41B characteristically have different extensibilities when stretched. Specifically, in a case where the elongation of the upper region 41 of the leak-proof cuff 28 in a natural state is defined as 0, and the elongation in a maximum stretched state is defined as 100, the stress σ1 of the first region 41A is larger than the stress σ2 of the second region 41B at an elongation of 5. At an elongation of 100, the stress σ2 of the second region 41B is larger than the stress σ1 of the first region 41A. This relation is represented by the graph shown in FIG. 6.

The upper region 41 in a natural state having an elongation of 0 means the state in which all the leak-proof cuff-forming elastic members 29 in the upper region 41 are not stretched and the upper region 41 has a minimum length. In the upper region 41, especially, the upper region 41 at a position with the leak-proof cuff-forming elastic member 29 located closest to the free edge 28B has a minimum length. The length of the upper region 41 at a position with the leak-proof cuff-forming elastic member 29 located closest to the free edge 28B is L1. L1 is on an extended line of the leak-proof cuff-forming elastic member 29. When only the upper region 41 is cut out from a leak-proof cuff 28, then the upper region 41 is bisected into the first region 41A and the second region 41B, and the first and second regions are separately measured, the first region 41A and the second region 41B may have different lengths. Even in the case, L1 is regarded as the length at an elongation of 0.

Figure 6:
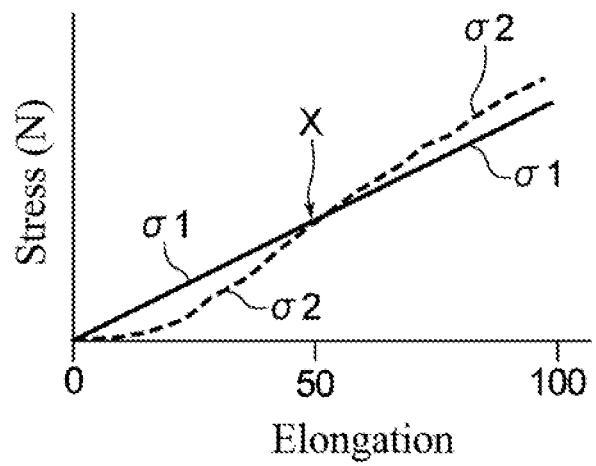
FIG. 6 is a graph showing the relation between elongation percentage and stress of the elastic members attached to a leak-proof cuff.

As shown in FIG. 6, the stress σ1 of the first region 41A is larger than the stress σ2 of the second region 41B at an elongation of 5. As the elongation gradually increases, both the stresses σ1 and σ2 increase, but the increasing rate differs between them. Specifically, the stress σ1 has a small slope in the graph and has a small increasing rate, and thus the stress σ1 does not greatly increase even when the elongation greatly increases. In contrast, the stress σ2 has a large slope in the graph and has a large increasing rate, and thus the stress σ2 greatly increases when the elongation greatly increases. As a result, the stresses σ1 and σ2 are equal at a particular elongation of X. At an elongation larger than X, the relation between the stresses σ1 and σ2 is reversed, and the stress σ2 becomes larger than the stress σ1.

The stress σ1 of the first region 41A and the stress σ2 of the second region 41B have such a relation, and thus the diaper 1 achieves the following advantageous effects: the contact condition of the leak-proof cuffs 28 with the legs of a wearer is stably maintained, and a clearance that may cause liquid leakage is unlikely to be formed between them even when the posture of the wearer changes, and the distance between the diaper 1 and the legs of the wearer changes accordingly. In addition, when the diaper 1 is worn, the stress σ1 of the first region 41A is not excessively high, and thus an excess increase of the wearing pressure applied onto the legs of a wearer is effectively prevented. As a result, an appropriate wearing pressure can be applied to the legs of a wearer depending on the distance between the diaper 1 and the legs of the wearer, and thus the physical burden on the wearer is reduced. If the wearing pressure is simply increased, the clearance can be prevented from generating. In contrast with such a concept, in the present invention, the above relation between the stress σ1 of the first region 41A and the stress σ2 of the second region 41B is satisfied, and accordingly a necessary and sufficient wearing pressure can be applied onto the legs of a wearer. This will be described with reference to FIG. 7 and FIG. 8.

Figure 7:
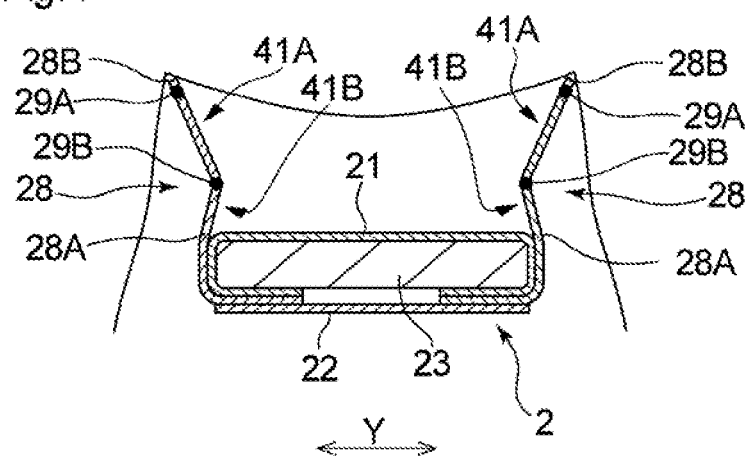
FIG. 7 is a schematic view showing a state of a crotch part of the diaper shown in FIG. 1 worn on a wearer.

FIG. 7 schematically shows the state of a crotch part when the diaper 1 is worn on a wearer. The state shown in the figure is a state in which the body of a wearer is distant from the absorbent assembly 2 due to a posture of the wearer. In such a state, the leak-proof cuffs 28 commonly have a small elongation. Accordingly, when the stress σ1 of the first region 41A is compared with the stress σ2 of the second region 41B, σ1>σ2. As a result, the first region 41A will be more strongly contracted than the second region 41B, and thus the leak-proof cuff 28 rises such that the first elastic member 29A in the first region 41A reaches the highest position as shown in FIG. 7. Hence, the position of the first elastic member 29A in the leak-proof cuff 28 is in appropriate contact with the vicinity of the groin of a wearer, and a clearance is unlikely to be formed between the legs of the wearer and the leak-proof cuffs 28. The liquid leakage is therefore effectively prevented.

Figure 8:
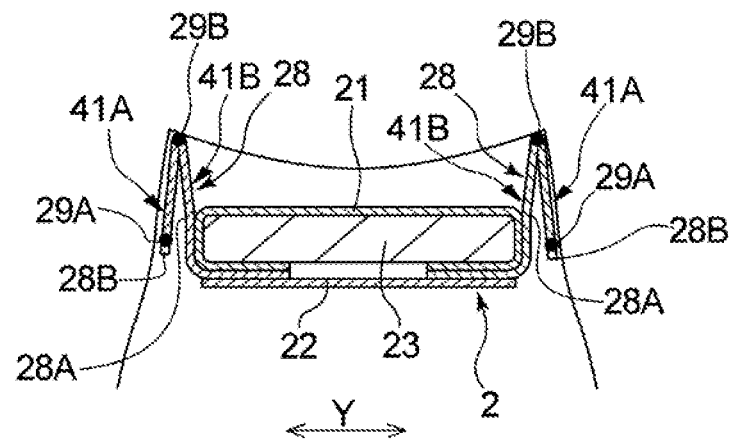
FIG. 8 is a schematic view showing another state of the crotch part of the diaper shown in FIG. 1 worn on a wearer.

Meanwhile, the state shown in FIG. 8 is a state in which the body of a wearer is close to the absorbent assembly 2 due to a posture of the wearer. In such a state, the leak-proof cuffs 28 commonly have a large elongation. Accordingly, when the stress σ1 of the first region 41A is compared with the stress σ2 of the second region 41B, σ1<σ2. As a result, the second region 41B will be more strongly contracted than the first region 41A, and thus the leak-proof cuff 28 rises such that the second elastic member 29B in the second region 41B reaches the highest position as shown in FIG. 8. Hence, the position of the second elastic member 29B in the second region 41B of the leak-proof cuff 28 is in appropriate contact with the groin of a wearer, and a clearance is unlikely to be formed between the legs of the wearer and the leak-proof cuffs 28. The liquid leakage is therefore effectively prevented. In addition, the increasing rate of the stress σ1 of the first region 41A is small as described above, and thus even when the body of a wearer becomes close to the absorbent assembly 2, the first region 41A is in contact with the legs of the wearer at a low wearing pressure. Hence, the leak-proof cuffs 28 do not apply an excessively high wearing pressure onto the legs of the wearer as a whole.

As described above, according to the diaper 1 of the present embodiment, the position of the leak-proof cuffs 28 in contact with the groin of a wearer changes depending on the distance between the diaper 1 and the body of the wearer wearing the diaper 1, and thus the contact condition of the leak-proof cuffs 28 with the legs of the wearer is stably maintained. From the viewpoint of more markedly achieving the effect, in a range of an elongation of 6 or more and 70 or less, especially, in a range of an elongation of 7 or more and 65 or less, the relation between the stress σ1 of the first region 41A and the stress σ2 of the second region 41B is preferably reversed. The relation between the stress σ1 of the first region 41A and the stress σ2 of the second region 41B can be appropriately adjusted, for example, by various means described later.

The above-described "elongation" is defined as follows. When all the leak-proof cuff-forming elastic members 29 in the upper region 41 are not stretched and have a minimum length, in the upper region 41, the leak-proof cuff 28 at a position with the leak-proof cuff-forming elastic member 29 located closest to the free edge 28B has the smallest length as described above. In the condition, when the length in a natural state of the leak-proof cuff 28 at a position with the leak-proof cuff-forming elastic member 29 located closest to the free edge 28B is L1, and the length in a maximum stretched state is L2, the elongation at any length L between L1 and L2 is represented by $[(L-L1)/(L2-L1)] \times 100$. The length in a maximum stretched state means the length of the first region 41A and the second region 41B determined when the first and second elastic members 29A and 29B are removed from the first region 41A and the second region 41B.

The stress σ1 of the first region 41A and the stress σ2 of the second region 41B are determined by the following procedure.
(1) From a leak-proof cuff 28, the upper region 41 is cut out. The upper region 41 is bisected along the center in the width direction Y into a first region 41A and a second region 41B as measurement sheets.
(2) For each measurement sheet, regions with no elastic members located at both ends in the longitudinal direction X are gripped at positions 10 mm apart from the ends by chucks of a Tensilon universal tester (RTC-1210A) manufactured by ORIENTEC CORPORATION.
(3) Each measurement sheet is pulled upward at a speed of 300 mm/min until the elongation reaches 100, and the going stress at an elongation of 5 and the stress at an elongation of 100 are determined. For an elongation of 100, the stress of each of the first region 41A and the second region 41B is determined when the chuck distance reaches a value calculated by subtraction of a gripping distance of 20 mm from the length L2 at a maximum stretched state.

From the viewpoint of bringing the leak-proof cuffs 28 into appropriate contact with the groin of a wearer independent of the distance between the diaper 1 and the body of the wearer, in a natural state, that is, at an elongation of 0, the length La of the first region 41A at a position with the first elastic member 29A located closest to the free edge 28B in the first region 41A is preferably smaller than the length Lb of the second region 41B at a position with the second elastic member 29B located closest to the folding line 42 in the second region 41B. In other words, it is preferable that La<Lb. With such a structure, the leak-proof cuffs 28 rise more smoothly, and especially in the state shown in FIG. 7, the leak-proof cuffs 28 are in appropriate contact with the groin of a wearer. From the viewpoint of more markedly achieving the effect, the value Lb/La is preferably 1.01 or more and 2.00 or less and more preferably 1.01 or more and 1.50 or less. When three or more leak-proof cuff-forming elastic members 29 are provided in the upper region 41 of a leak-proof cuff 28, the length of the leak-proof cuff 28 with the leak-proof cuff-forming elastic members 29 preferably decreases gradually from the elastic member located closest to the folding line 42 to the elastic member located closest to the free edge 28B. The length may reduce continuously or may reduce step-by-step.

La and Lb are determined by the following procedure.
(1) A leak-proof cuff 28 is cut along the folding line 42 to cut out the upper region 41. When an elastic member is provided on the folding line 42, the elastic member is regarded as the second elastic member 29B, and the leak-proof cuff 28 is cut such that the elastic member is included in the second region 41B. The upper region 41 is further bisected along the center in the width direction of the upper region 41 into a first region 41A and a second region 41B as measurement sheets. When an elastic member is provided along the center in the width direction of the upper region 41, the elastic member is regarded as the first elastic member 29A and the second elastic member 29B, and two upper regions are cut as follows: one upper region is cut such that the elastic member is included in the first region 41A; and the other upper region is cut such that the elastic member is included in the second region 41B, giving two pairs of measurement sheets.
(2) The respective measurement sheets are linearly spread to such an extent that the first and second elastic members 29A and 29B express no contraction force. At this time, the measurement sheet can be attached to a table with an adhesive tape or the like.
(3) For each measurement sheet, the length of a minimum part from one end to the other end of the measurement sheet at a position with the first or second elastic member 29A or 29B is determined. The minimum part is located above the extended line of the first or second elastic member 29A or 29B.
(4) The measurement in accordance with (1) to (3) is performed three times, and the average of three measurement results of the length of the minimum part of the measurement sheet at a position with the first or second elastic member 29A or 29B determined in (3) is calculated as La or Lb, respectively.

In order to satisfy the above relation between La and Lb, for example, in the leak-proof cuff 28, the extension rate Sa of the elastic member 29A located closest to the free edge 28B of the first elastic members 29A provided in the first region 41A is preferably higher than the extension rate Sb of the second elastic member 29B located closest to the folding line 42 in the second region 41B of the leak-proof cuff-forming elastic members 29 in the upper region 41. In particular, when a plurality of second elastic members 29B are provided in the second region 41B, the extension rate Sa of the elastic member 29A located closest to the free edge 28B of the first elastic members 29A provided in the first region 41A is preferably higher than the extension rates Sb of all the second elastic members 29B provided in the second region 41B. In particular, the value Sa/Sb is preferably 1.01 or more and 1.80 or less and more preferably 1.01 or more and 1.60 or less. In order to set Sa larger than Sb, while the first elastic member 29A is stretched at a higher extension rate than that of the second elastic member 29B, the first elastic member 29A and the second elastic member 29B can be attached to a leak-proof cuff 28. When three or more leak-proof cuff-forming elastic members 29 are provided in the upper region 41 of a leak-proof cuff 28, the extension rate Sa of the first elastic member 29A located closest to the free edge 28B in the first region 41A is preferably higher than the extension rates Sb of all the second elastic members 29B in the second region 41B. The extension rate of the leak-proof cuff-forming elastic member 29 more preferably increases gradually from the elastic member located closest to the folding line 42 to the elastic member located closest to the free edge 28B. In this case, the extension rate may increase continuously or may increase step-by-step.

Sa and Sb are determined by the following procedure.
(1) Each of the first region 41A and the second region 41B is fixed while stretched into a length in a maximum stretched state, and the length of an elasticized region in which the first or second elastic member 29A or 29B is fixed to the leak-proof cuff 28 with an adhesive or the like is determined. The length of an elasticized region is a distance between the fixed ends of each of the first and second elastic members 29A and 29B. The fixed ends are located at the respective ends of the first or second elastic member 29A or 29B in the longitudinal direction X and are ends in a region in which the elastic member is fixed to the leak-proof cuff 28.
(2) The first and second elastic members 29A and 29B are cut in the respective ends of the regions in which these elastic members 29A and 29B are fixed to the leak-proof cuff 28, and these elastic members 29A and 29B are extracted from the leak-proof cuff 28 by using ethanol or the like.
(3) The natural lengths of the first and second elastic members 29A and 29B are determined while the elastic members are linearly spread to such an extent that no contraction force is expressed. For the measurement, the extracted first and second elastic members 29A and 29B can be attached to a table with an adhesive tape or the like.
(4) The length of an elasticized region determined in (1) is divided by the natural length of the first or second elastic member 29A or 29B determined in (3), giving the extension rates Sa and Sb.

In order to allow the leak-proof cuff 28 to rise more smoothly, of the leak-proof cuff-forming elastic members 29 in the upper region 41, the first elastic member 29A located closest to the free edge 28B in the first region 41A preferably has the longest fixed length to the leak-proof cuff 28. When three or more leak-proof cuff-forming elastic members 29 are provided in the upper region 41 of a leak-proof cuff 28, at least the first elastic member 29A located closest to the free edge 28B in the first region 41A preferably has the longer fixed length to the leak-proof cuff 28 than that of the second elastic member 29B in the second region 41B. The fixed lengths of the leak-proof cuff-forming elastic members 29 located in the upper region 41 preferably increase gradually from the elastic member located closest to the folding line 42 to the elastic member located closest to the free edge 28B. The lengths may increase continuously or may increase step-by-step. In this case, all the leak-proof cuff-forming elastic members 29 in the upper region 41 are preferably across at least the crotch portion 1B. The fixed ends of the leak-proof cuff-forming elastic members 29 in the upper region 41 are preferably located sequentially outward in the longitudinal direction X from the elastic member located closest to the folding line 42 to the elastic member located closest to the free edge 28B. The fixed end is as defined above.

As for the fixed ends of the leak-proof cuff-forming elastic member 29 provided in the upper region 41, at least one fixed end of the two fixed ends is preferably located longitudinally inside from a longitudinal front edge or a longitudinal rear edge of the absorbent core from the viewpoint of allowing the absorbent core to be unlikely to deform against the contraction force of the leak-proof cuff-forming elastic member 29 provided in the upper region 41. From this viewpoint, both the fixed ends of the leak-proof cuff-forming elastic member 29 provided in the upper region 41 are preferably located longitudinally inside from the longitudinal front edge or the longitudinal rear edge of the absorbent core in the longitudinal direction X. From the same viewpoint, the fixed ends of all the leak-proof cuff-forming elastic members 29 provided in the upper region 41 are preferably located longitudinally inside from the longitudinal front edge or the longitudinal rear edge of the absorbent core.

From the viewpoint of bringing the leak-proof cuffs 28 into appropriate contact with the groin of a wearer independent of the distance between the diaper 1 and the body of the wearer, of the leak-proof cuff-forming elastic members 29 provided in the upper region 41, the modulus Mb of the second elastic member 29B located closest to the folding line 42 in the second region 41B is preferably higher than the modulus Ma of the first elastic member 29A located closest to the free edge 28B in the first region 41A. The modulus is a tensile stress of an object that resists an external force for holding the original shape thereof. When Ma<Mb, the second elastic member 29B can easily have a larger modulus Mb in a region in which the leak-proof cuff 28 has a large elongation. From this viewpoint, the value Mb/Ma is preferably 1.01 or more and 2.00 or less and more preferably 1.01 or more and 1.80 or less. In order set Mb larger than Ma, an isoprene rubber exhibiting a high repulsion elasticity is used as the second elastic member 29B, or a styrene-butadiene rubber thread exhibiting a low repulsion elasticity is used as the first elastic member 29A, as an example method. When three or more leak-proof cuff-forming elastic members 29 are provided in the upper region 41 of a leak-proof cuff 28, the modulus Ma of at least the first elastic member 29A located closest to the free edge 28B in the first region 41A is preferably lower than the moduli of all the second elastic members 29B provided in the second region 41B. In addition, the moduli of the leak-proof cuff-forming elastic members 29 preferably increase gradually from the elastic member located closest to the free edge 28B to the elastic member located closest to the folding line 42. In this case, the moduli may increase continuously or may increase step-by-step.

The above "modulus" is defined by the following procedure. Each leak-proof cuff-forming elastic member 29 provided in the upper region 41 is extracted from the leak-proof cuff 28. The natural length of the extracted leak-proof cuff-forming elastic member 29 is LE1. A length twice the length LE1 is LE2. When the leak-proof cuff-forming elastic member 29 is pulled to a length of LE1.5 that is 1.5 times LE1, the stress is determined as SE1.5, and when the elastic member is pulled to a length of LE2, the stress is determined as SE2. The value (SE2)/(SE1.5) as the ratio between SE1.5 and SE2 is an index of the modulus Ma or Mb.

The moduli Ma and Mb are determined by the following procedure.
(1) From a leak-proof cuff 28, a leak-proof cuff-forming elastic member 29 is extracted by using ethanol or the like.
(2) The leak-proof cuff-forming elastic member 29 is linearly spread to such an extent that no contraction force is expressed. An inside position 10 mm apart from each end of the leak-proof cuff-forming elastic member 29 is marked as a gripping position, and the natural length (LE1) of an elasticized region between the marks is determined.
(3) The leak-proof cuff-forming elastic member 29 is gripped at positions 10 mm apart from the ends by a Tensilon universal tester (RTC-1210A) manufactured by ORIENTEC CORPORATION and is pulled upward at a speed of 300 mm/min until the chuck distance reaches twice the natural length of the elasticized region of the leak-proof cuff-forming elastic member 29 (LE2), and the stress is determined (SE2).
(4) The leak-proof cuff-forming elastic member 29 is pulled to 1.5 times the natural length of the elasticized region (LE1.5), and the stress is determined (SE1.5). The value (SE2)/(SE1.5) as the ratio between SE2 and SE1.5 is calculated.

In the above measurement, the natural length (LE1) of the elasticized region of each leak-proof cuff-forming elastic member 29 may be adjusted to the same length. For example, when the natural length (LE1) of an elasticized region is 70 mm, a leak-proof cuff-forming elastic member 29 can be cut out such that the elastic member 29 including the gripping positions has a length of 90 mm, then each end portion having a length of 10 mm can be gripped, and the elastic member can be pulled until the chuck distance reaches twice the natural length (LE1=70 mm) of the elasticized region of the elastic member 29 (LE2=140 mm).

Of the leak-proof cuff-forming elastic members 29 provided in the upper region 41, the thickness Db of the second elastic member 29B located closest to the folding line in the second region 41B is preferably larger than the thickness Da of the first elastic member 29A located closest to the free edge 28B in the first region 41A from the viewpoint of bringing the leak-proof cuffs 28 into appropriate contact with the groin of a wearer independent of the distance between the diaper 1 and the body of the wearer. When Da<Db, the second region 41B can be strongly contracted in a region having a larger elongation in the leak-proof cuff 28. From this viewpoint, the value Db/Da is preferably 1.30 or more and 3.00 or less and more preferably 1.50 or more and 2.60 or less. When three or more leak-proof cuff-forming elastic members 29 are provided in the upper region 41 of a leak-proof cuff 28, the thicknesses of all the second elastic members 29B provided in the second region 41B are preferably larger than the thickness Da of at least the first elastic member 29A located closest to the free edge 28B in the first region 41A. The leak-proof cuff-forming elastic members 29 in the upper region 41 may have various thicknesses. In this case, the thicknesses of the leak-proof cuff-forming elastic members 29 preferably increase gradually from the elastic member located closest to the free edge 28B to the elastic member located closest to the folding line 42. The thicknesses may increase continuously or may increase step-by-step.

From a similar viewpoint to the above, when three of more leak-proof cuff-forming elastic members 29 extending along the longitudinal direction X are provided in a stretched state in an upper region 41, the number Nb of the second elastic members 29B located in the second region 41B is preferably larger than the number Na of the first elastic members 29A located in the first region 41A. In particular, the value Nb/Na is preferably more than 1 and not more than 3 and more preferably more than 1 and not more than 2. When a leak-proof cuff-forming elastic member 29 is provided at the center in the width direction Y in an upper region 41, unlike the above case of the measurement of La and Lb, the elastic member 29 is counted as the number Nb of second elastic members 29B in the second region 41B.

As with the above, when three of more leak-proof cuff-forming elastic members 29 extending along the longitudinal direction X are provided in a stretched state in an upper region 41, the intervals between all the adjacent leak-proof cuff-forming elastic members 29 are preferably the same, or the intervals preferably decrease as a leak-proof cuff-forming elastic member 29 is closer to the folding line 42. In the latter case, two leak-proof cuff-forming elastic members 29 adjacent at a small interval elastically behave spuriously similar to a single leak-proof cuff-forming elastic member 29, and thus the leak-proof cuff-forming elastic members 29 provided in the second region 41B can be strongly contracted in a region having a large elongation in the leak-proof cuff 28.

Figure 9A:
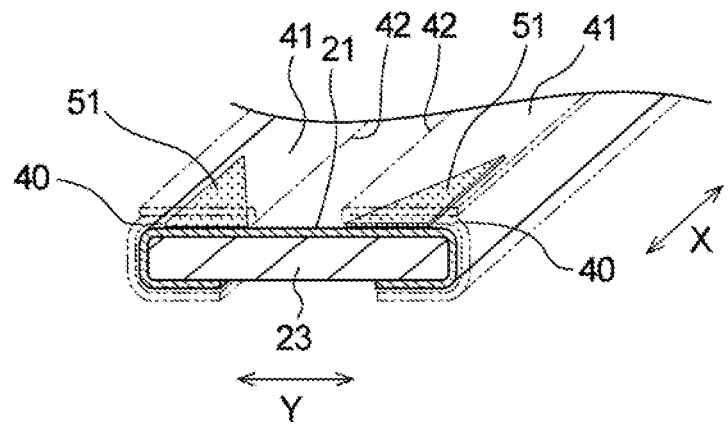
FIGS. 9(a) to (c) are perspective views each showing joined regions between a lower region of a leak-proof cuff and a topsheet.
Figure 9B:
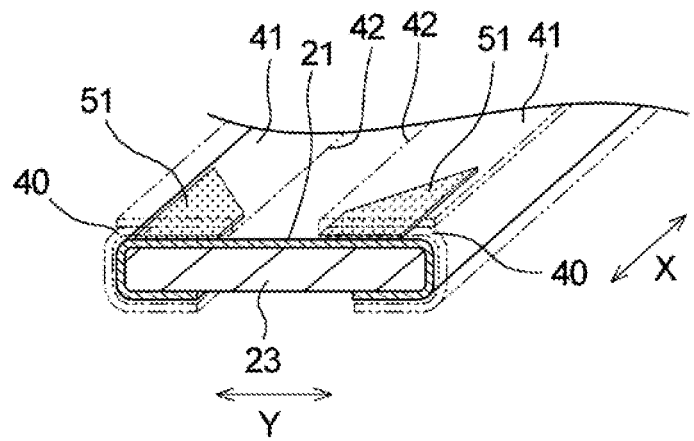
Figure 9C:
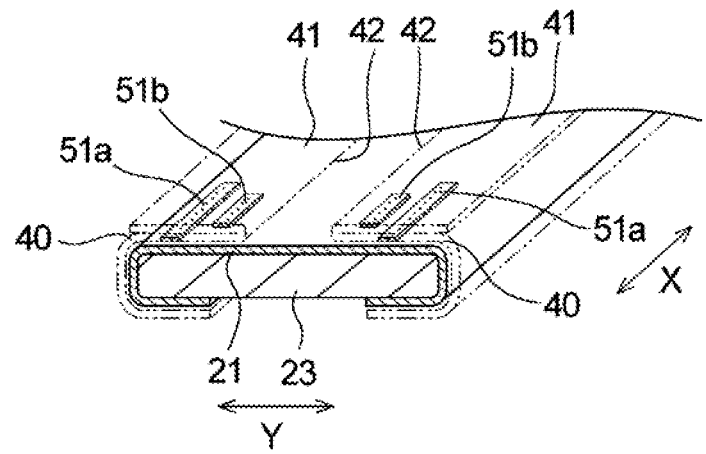

As described above, the inner face of the lower region 40 of the leak-proof cuff 28 is joined to the skin-facing surface of the topsheet 21 through the first joined regions 51. In this case, the length of the first joined region 51 in the longitudinal direction X preferably increases from the inside to the outside in the width direction Y as shown in FIG. 9(a). The figure shows the state in which the length in the longitudinal direction X gradually increases from the inside to the outside in the width direction Y. With such a structure, the lower region 40 rises more smoothly. In the embodiment shown in FIG. 9(a), the length of the first joined region 51 in the longitudinal direction X is 0 at the innermost side in the width direction Y. Alternatively, as shown in FIG. 9(b), the length of a first joined region 51 in the longitudinal direction X may be a predetermined value more than 0 at the innermost side in the width direction Y In the embodiments shown in FIGS. 9(a) and (b), the first joined region 51 is continuously formed in the width direction Y. Alternatively, as shown in FIG. 9(c), a first joined region 51 may be divided into two joined regions 51a and 51b, the joined regions 51a and 51b may be formed discontinuously in the width direction Y, and the length in the longitudinal direction X may increase from the inside to the outside in the width direction Y in terms of the whole first joined region 51. Of the two joined regions 51a and 51b, the joined region 51a located outside in the width direction Y is longer than the joined region 51b located inside.

Figure 10A:
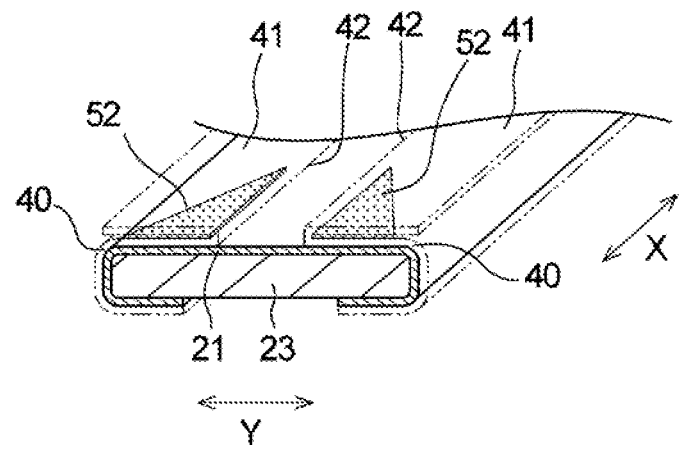
FIGS. 10(a) to (c) are perspective views each showing joined regions between a lower region and an upper region of a leak-proof cuff.
Figure 10B:
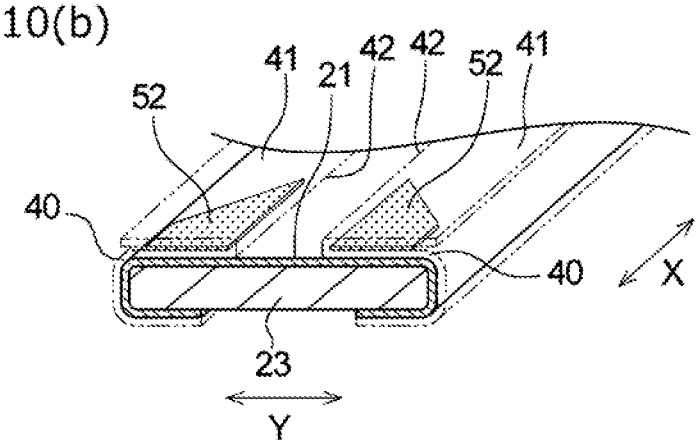
Figure 10C:
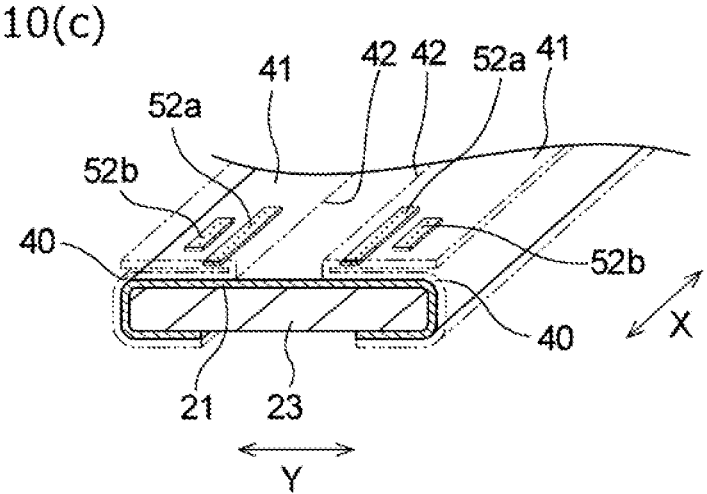

As for the second joined regions 52, as shown in FIG. 10(a), the length in the longitudinal direction X preferably increases from the outside to the inside in the width direction Y. The figure shows the state in which the length in the longitudinal direction X gradually increases from the outside to the inside in the width direction Y. With such a structure, the upper region 41 rises more smoothly. In the embodiment shown in FIG. 10(a), the length of the second joined region 52 in the longitudinal direction X is 0 at the outermost side in the width direction Y. Alternatively, as shown in FIG. 10(b), the length of a second joined region 52 in the longitudinal direction X may be a predetermined value more than 0 at the outermost side in the width direction Y. In the embodiments shown in FIGS. 10(a) and (b), the second joined region 52 is continuously formed in the width direction Y. Alternatively, as shown in FIG. 10(c), a second joined region 52 may be divided into two joined regions 52a and 52b, the joined regions 52a and 52b may be formed discontinuously in the width direction Y, and the length in the longitudinal direction X may increase from the outside to the inside in the width direction Y in terms of the whole second joined region 52. Of the two joined regions 52a and 52b, the joined region 52a located inside in the width direction Y is longer than the joined region 52b located outside.

Figure 11:
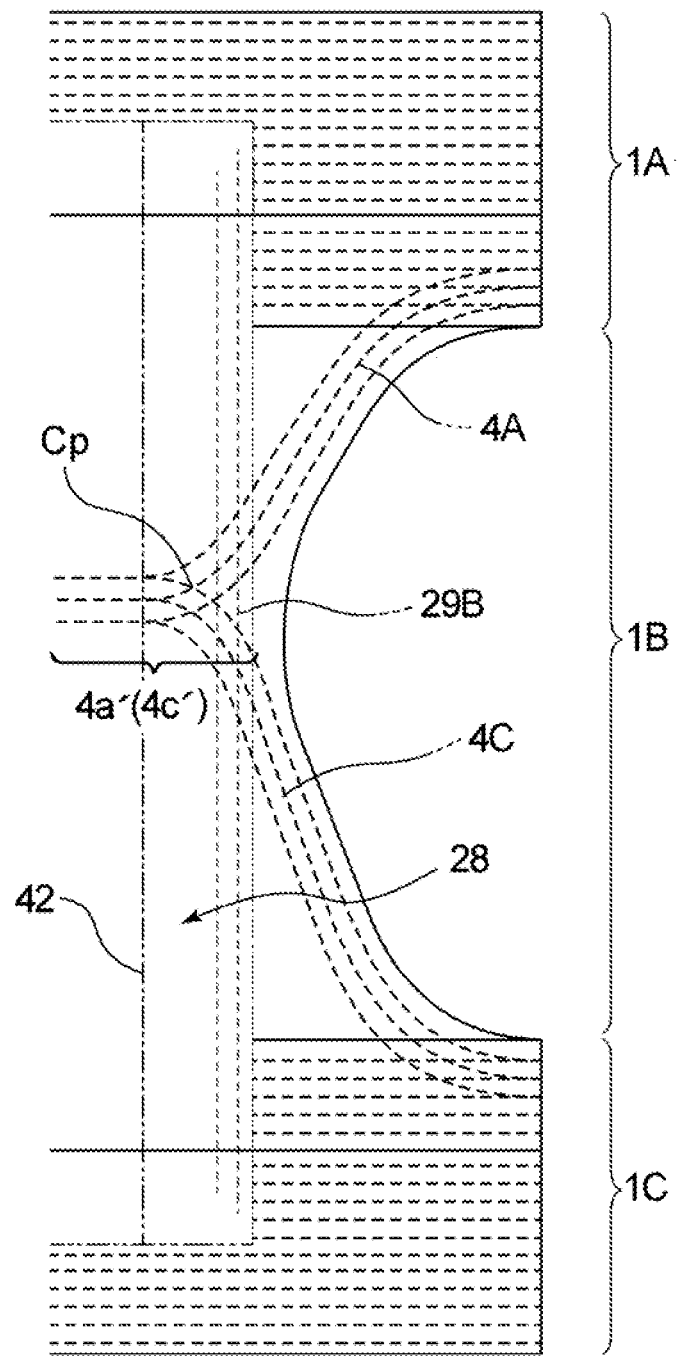
FIG. 11 is an enlarged plan view of a principal part of a crotch portion of the diaper shown in FIG. 1.

FIG. 11 shows an enlarged principal part of the crotch portion 1B of the diaper 1. The figure is a planar view of the diaper 1 in its flat-out, uncontracted state. As shown in the figure, one end of each of the front portion leg elastic members 4A and the rear portion leg elastic members 4C terminates at a position on the corresponding side edge of the front portion 1A or the rear portion 1C, and other end regions 4a' and 4c' including the other ends extend inward in the width direction Y in the crotch portion 1B. The other end region 4a' of the front portion leg elastic member 4A and the other end region 4c' of the rear portion leg elastic member 4C intersect with each other in the crotch portion 1B. The front portion leg elastic members 4A and the rear portion leg elastic members 4C overlap with the leak-proof cuff-forming elastic members 29 at the crotch portion 1B in the thickness direction. With such a structure, due to the contraction of the front portion leg elastic members 4A and the rear portion leg elastic members 4C, the leak-proof cuff-forming elastic members 29 are allowed to rise toward the body of a wearer, and thus a clearance is more unlikely to be formed between the leak-proof cuffs 28 and the body of a wearer. Intersection points Cp between the front portion leg elastic members 4A and the rear portion leg elastic members 4C overlapping at the crotch portion 1B in the thickness direction are located inside in the width direction Y from the first elastic member 29A located closest to the free edge 28B in the first region 41A of the leak-proof cuff-forming elastic members 29 of the leak-proof cuff 28.

The embodiment shown in FIG. 11 includes a plurality of intersection points Cp between the front portion leg elastic members 4A in the other end region 4a' and the rear portion leg elastic members 4C in the other end region 4c'. In this case, at least one of the plurality of intersection points Cp can be located inside in the width direction Y from the first elastic member 29A located closest to the free edge 28B in the first region 41A. The state shown in FIG. 11 may be satisfied in a natural state of the diaper 1. In other words, the state shown in FIG. 11 can be satisfied in at least one of the natural state and the stretched state of the diaper 1.

The present invention has been described on the basis of the preferred embodiments thereof, but the present invention is not limited to the above embodiments. For example, in the above embodiments, the absorbent article of the present invention is applied to a pull-on disposable diaper. Alternatively, the present invention can be applied to an open type disposable diaper. The present invention can also be applied to other absorbent articles than the disposable diaper, such as a sanitary napkin and an incontinence pad.

In consideration of the above embodiments, the present invention further discloses the following absorbent articles.

<1> An absorbent article comprising:
leak-proof cuffs extending along a longitudinal direction and located at side regions in a width direction of the absorbent article, wherein
the leak-proof cuff is folded on a folding line extending along the longitudinal direction of the leak-proof cuff and is divided into an upper region and a lower region at the folding line,
in the leak-proof cuff folded on the folding line, the folding line is located inside in the width direction from a free edge of the leak-proof cuff,
the upper region includes a first region located at a side of the free edge relative to a center of the upper region in the width direction and a second region located at a side of the folding line,
in each of the first region and the second region, at least one elastic member extending along the longitudinal direction is provided in a stretched state,
in a case where an elongation of the upper region in a natural state is defined as 0, and an elongation in a maximum stretched state is defined as 100,
a stress σ1 of the first region is larger than a stress σ2 of the second region at an elongation of 5, and
the stress σ2 of the second region is larger than the stress σ1 of the first region at an elongation of 100.

<2> The absorbent article as set forth in clause <1>, wherein, in a range of an elongation of 6 or more and 70 or less, a relation between the stress σ1 of the first region and the stress σ2 of the second region is reversed.

<3> The absorbent article as set forth in clause <2>, wherein, in a range of an elongation of 7 or more and 65 or less, the relation between the stress σ1 of the first region and the stress σ2 of the second region is reversed.

<4> The absorbent article as set forth in any one of clauses <1> to <3>, in a natural state, a length of the first region at a position with an elastic member located closest to the free edge is shorter than a length of the second region at a position with an elastic member located closest to the folding line.

<5> The absorbent article as set forth in any one of clauses <1> to <4>, wherein, in a natural state, a ratio Lb/La is preferably 1.01 or more and 2.00 or less and more preferably 1.01 or more and 1.50 or less, where Lb is a length of the second region at a position with the elastic member located closest to the folding line in the second region, and La is a length of the first region at a position with the elastic member located closest to the free edge in the first region.

<6> The absorbent article as set forth in any one of clauses <1> to <5>, wherein three or more elastic members are provided in the upper region of the leak-proof cuff, and
  a length of the leak-proof cuff at positions with the elastic members gradually decreases from the elastic member located closest to the folding line to the elastic member located closest to the free edge.

<7> The absorbent article as set forth in any one of clauses <1> to <6>, wherein, of the elastic members, the elastic member located closest to the free edge in the first region has a higher extension rate than an extension rate of the elastic member located closest to the folding line in the second region.

<8> The absorbent article as set forth in any one of clauses <1> to <7>, wherein three or more elastic members extending along the longitudinal direction are provided in a stretched state in the upper region,
  the elastic member located closest to the free edge in the first region has a higher extension rate than extension rates of all the elastic members provided in the second region, and
  the extension rates of the elastic members gradually increase from the elastic member located closest to the folding line to the elastic member located closest to the free edge.

<9> The absorbent article as set forth in any one of clauses <1> to <8>, wherein a ratio Sa/Sb is preferably 1.01 or more and 1.80 or less and more preferably 1.01 or more and 1.60 or less, where Sa is the extension rate of the elastic member located closest to the free edge in the first region, and Sb is the extension rate of the elastic member located closest to the folding line in the second region.

<10> The absorbent article as set forth in any one of clauses <1> to <9>, wherein the extension rates of the elastic members gradually increase from the elastic member located closest to the folding line to the elastic member located closest to the free edge.

<11> The absorbent article as set forth in any one of clauses <1> to <10>, wherein, of the elastic members, the elastic member located closest to the folding line in the second region has a higher modulus than a modulus of the elastic member located closest to the free edge in the first region.

<12> The absorbent article as set forth in any one of clauses <1> to <11>, wherein a ratio Mb/Ma is preferably 1.01 or more and 2.00 or less and more preferably 1.01 or more and 1.80 or less, where Mb is a modulus of the elastic member located closest to the folding line in the second region, and Ma is a modulus of the elastic member located closest to the free edge in the first region.

<13> The absorbent article as set forth in any one of clauses <1> to <12>, wherein three or more elastic members are provided in the upper region of the leak-proof cuff, and
  the modulus Ma of at least the elastic member located closest to the free edge in the first region is lower than the moduli of all the elastic members provided in the second region.

<14> The absorbent article as set forth in any one of clauses <1> to <13>, wherein the moduli of the elastic members gradually increase from the elastic member located closest to the free edge to the elastic member located closest to the folding line.

<15> The absorbent article as set forth in any one of clauses <1> to <14>, wherein, of the elastic members, the elastic member located closest to the folding line in the second region is thicker than the elastic member located closest to the free edge in the first region.

<16> The absorbent article as set forth in any one of clauses <1> to <15>, wherein three or more elastic members extending along the longitudinal direction are provided in a stretched state in the upper region,
  all the elastic members provided in the second region are thicker than the elastic member located closest to the free edge in the first region, and
  the thicknesses of the elastic members gradually increase from the elastic member located closest to the free edge to the elastic member located closest to the folding line.

<17> The absorbent article as set forth in any one of clauses <1> to <16>, wherein a ratio Db/Da is preferably 1.30 or more and 3.00 or less and more preferably 1.50 or more and 2.60 or less, where Db is the thickness of the elastic member located closest to the folding line in the second region, and Da is the thickness of the elastic member located closest to the free edge in the first region.

<18> The absorbent article as set forth in any one of clauses <1> to <17>, wherein the thicknesses of the elastic members gradually increase from the elastic member located closest to the free edge to the elastic member located closest to the folding line.

<19> The absorbent article as set forth in any one of clauses <1> to <18>, wherein three or more elastic members extending along the longitudinal direction are provided in a stretched state in the upper region, and
  a larger number of elastic members are located in the second region than the number of elastic members located in the first region.

<20> The absorbent article as set forth in any one of clauses <1> to <19>, wherein a ratio Nb/Na is preferably more than 1 and not more than 3 and more preferably more than 1 and not more than 2, where Nb is the number of the elastic members located in the second region, and Na is the number of the elastic members located in the first region.

<21> The absorbent article as set forth in any one of clauses <1> to <20>, wherein intervals between all the adjacent elastic members located in the upper region are identical, or the intervals decrease as adjacent elastic members are closer to the folding line.

<22> The absorbent article as set forth in any one of clauses <1> to <21>, wherein, of the elastic members, the elastic member located closest to the free edge has the longest fixed length to the leak-proof cuff.

<23> The absorbent article as set forth in any one of clauses <1> to <22>, wherein the fixed lengths of the elastic members located in the upper region gradually increase from the elastic member located closest to the folding line to the elastic member located closest to the free edge.

<24> The absorbent article as set forth in any one of clauses <1> to <23>, wherein fixed ends of the elastic members in the upper region are located sequentially outward in the longitudinal direction from the elastic member located closest to the folding line to the elastic member located closest to the free edge.

<25> The absorbent article as set forth in any one of clauses <1> to <24>, wherein the elastic member has fixed ends which are located at longitudinal ends of the elastic member and at which the leak-proof cuff are fixed, and
  at least one of the fixed end is located longitudinally inside from a longitudinal front edge or a longitudinal rear edge of an absorbent core.

<26> The absorbent article as set forth in any one of clauses <1> to <25>, wherein the two fixed ends of the elastic member provided in the upper region are located longitudinally inside from a longitudinal front edge or a longitudinal rear edge of the absorbent core.

<27> The absorbent article as set forth in any one of clauses <1> to <26>, wherein the folding line is located above a topsheet.

<28> The absorbent article as set forth in any one of clauses <1> to <27>, wherein the folding line is located above an absorbent member.

<29> The absorbent article as set forth in any one of clauses <1> to <28>, wherein an inner face of the lower region is joined to the topsheet in an end region in the longitudinal direction to form a first joined region, and
a length of the first joined region in the longitudinal direction gradually increases from an inside to an outside in the width direction.

<30> The absorbent article as set forth in any one of clauses <1> to <29>, wherein an outer face of the lower region is joined to an outer face of the upper region at an end region in the longitudinal direction to form a second joined region.

<31> The absorbent article as set forth in clause <30>, wherein a length of the second joined region in the longitudinal direction gradually increases from an outside to an inside in the width direction.

<32> The absorbent article as set forth in any one of clauses <1> to <31>, wherein the free edge is located above a side edge of the absorbent member or located inside the side edge in the width direction.

<33> The absorbent article as set forth in any one of clauses <1> to <32>, wherein the absorbent article has a front portion to be placed on a front side of a wearer wearing the absorbent article, a rear portion to be placed on a rear side of the wearer, and a crotch portion located therebetween,
a front portion leg elastic member is provided along a leg opening located close to the front portion, a rear portion leg elastic member is provided along a leg opening located close to the rear portion,
one end of each of the front portion leg elastic member and the rear portion leg elastic member terminates at a position on a corresponding side edge of the front portion or the rear portion, and another end region including the other end extends inward in the width direction in the crotch portion.

<34> The absorbent article as set forth in clause <33>, wherein, in a plan view of the absorbent article in its flat-out, uncontracted state, the front portion leg elastic member and the rear portion leg elastic member overlap with the elastic members of the leak-proof cuff at the crotch portion in a thickness direction.

<35> The absorbent article as set forth in clause <33> or <34>, wherein, in a plan view of the absorbent article in its flat-out, uncontracted state, an intersection point between the front portion leg elastic member and the rear portion leg elastic member overlapping at the crotch portion in the thickness direction is located inside in the width direction from the elastic member located closest to the free edge in the first region of the elastic members of the leak-proof cuff.

<36> The absorbent article as set forth in any one of clauses <1> to <35>, wherein, in the lower region, no elastic member is provided.

INDUSTRIAL APPLICABILITY

As described above, according to the present invention, the contact condition of leak-proof cuffs with the legs of a wearer is stably maintained, and a clearance that may cause liquid leakage is unlikely to be formed between them even when the posture of the wearer changes, and the distance between the absorbent article and the legs of the wearer changes accordingly.

The invention claimed is:
1. An absorbent article comprising:
leak-proof cuffs extending along a longitudinal direction and located at side regions in a width direction of the absorbent article, wherein
the leak-proof cuff is folded on a folding line extending along the longitudinal direction of the leak-proof cuff and is divided into an upper region and a lower region at the folding line,
in the leak-proof cuff folded on the folding line, the folding line is located inside in the width direction from a free edge of the leak-proof cuff,
the upper region includes a first region located at a side of the free edge relative to a center of the upper region in the width direction and a second region located at a side of the folding line,
in each of the first region and the second region, at least one elastic member extending along the longitudinal direction is provided in a stretched state,
in a case where an elongation of the upper region in a natural state is defined as 0, and an elongation in a maximum stretched state is defined as 100,
a stress σ1 of the first region is larger than a stress σ2 of the second region at an elongation of 5, and
the stress σ2 of the second region is larger than the stress σ1 of the first region at an elongation of 100.

2. The absorbent article according to claim 1, wherein, in a natural state, a length of the first region at a position with an elastic member located closest to the free edge is shorter than a length of the second region at a position with an elastic member located closest to the folding line.

3. The absorbent article according to claim 1, wherein, of the elastic members, the elastic member located closest to the free edge in the first region has a higher extension rate than an extension rate of the elastic member located closest to the folding line in the second region.

4. The absorbent article according to claim 1, wherein, of the elastic members, the elastic member located closest to the folding line in the second region has a higher modulus than a modulus of the elastic member located closest to the free edge in the first region.

5. The absorbent article according to claim 1, wherein, of the elastic members, the elastic member located closest to the folding line in the second region is thicker than the elastic member located closest to the free edge in the first region.

6. The absorbent article according to claim 1, wherein three or more elastic members extending along the longitudinal direction are provided in a stretched state in the upper region, and
a larger number of elastic members are located in the second region than the number of elastic members located in the first region.

7. The absorbent article according to claim 1, wherein intervals between all the adjacent elastic members located in the upper region are identical, or the intervals decrease as adjacent elastic members are closer to the folding line.

8. The absorbent article according to claim 1, wherein, in a range of an elongation of 6 or more and 70 or less, a relation between the stress σ1 of the first region and the stress σ2 of the second region is reversed.

9. The absorbent article according to claim 1, wherein three or more elastic members extending along the longitudinal direction are provided in a stretched state in the upper region,
- the elastic member located closest to the free edge in the first region has a higher extension rate than extension rates of all the elastic members provided in the second region, and
- the extension rates of the elastic members gradually increase from the elastic member located closest to the folding line to the elastic member located closest to the free edge.

10. The absorbent article according to claim 1, wherein three or more elastic members extending along the longitudinal direction are provided in a stretched state in the upper region,
- all the elastic members provided in the second region are thicker than the elastic member located closest to the free edge in the first region, and
- the thicknesses of the elastic members gradually increase from the elastic member located closest to the free edge to the elastic member located closest to the folding line.

11. The absorbent article according to claim 1, wherein of the elastic members, the elastic member located closest to the free edge has a longest fixed length to the leak-proof cuff.

12. The absorbent article according to claim 1, wherein the folding line is located above a topsheet.

13. The absorbent article according to claim 1, wherein the folding line is located above an absorbent member.

14. The absorbent article according to claim 1, wherein the elastic member has fixed ends which are located at longitudinal ends of the elastic member and at which the leak-proof cuff are fixed, and
- at least one of the fixed end is located longitudinally inside from a longitudinal front edge or a longitudinal rear edge of an absorbent core.

15. The absorbent article according to claim 1, wherein an inner face of the lower region is joined to the topsheet at an end region in the longitudinal direction to form a first joined region, and
- a length of the first joined region in the longitudinal direction gradually increases from an inside to an outside in the width direction.

16. The absorbent article according to claim 1, wherein an outer face of the lower region is joined to an outer face of the upper region at an end region in the longitudinal direction to form a second joined region.

17. The absorbent article according to claim 16, wherein a length of the second joined region in the longitudinal direction gradually increases from an outside to an inside in the width direction.

18. The absorbent article according to claim 1, wherein the free edge is located above a side edge of the absorbent member or located inside the side edge in the width direction.

19. The absorbent article according to claim 1, wherein the absorbent article has a front portion to be placed on a front side of a wearer wearing the absorbent article, a rear portion to be placed on a rear side of the wearer, and a crotch portion located therebetween,
- a front portion leg elastic member is provided along a leg opening located close to the front portion, a rear portion leg elastic member is provided along a leg opening located close to the rear portion,
- one end of each of the front portion leg elastic member and the rear portion leg elastic member terminates at a position on a corresponding side edge of the front portion or the rear portion, and another end region including the other end extends inward in the width direction in the crotch portion.

20. An absorbent article comprising:
- leak-proof cuffs extending along a longitudinal direction and located at side regions in a width direction of the absorbent article, wherein
- the leak-proof cuff is folded on a folding line extending along the longitudinal direction of the leak-proof cuff and is divided into an upper region and a lower region at the folding line,
- in the leak-proof cuff folded on the folding line, the folding line is located inside in the width direction from a free edge of the leak-proof cuff,
- the upper region includes a first region located at a side of the free edge relative to a center of the upper region in the width direction and a second region located at a side of the folding line,
- in each of the first region and the second region, at least one elastic member extending along the longitudinal direction is provided in a stretched state,
- in a case where an elongation of the upper region in a natural state is defined as 0, and an elongation in a maximum stretched state is defined as 100,
- a stress σ1 of the first region is larger than a stress σ2 of the second region at an elongation of 5, and
- the stress σ2 of the second region is larger than the stress σ1 of the first region at an elongation of 100,
- wherein, of the elastic members, the elastic member located closest to the free edge in the first region has a higher extension rate than an extension rate of the elastic member located closest to the folding line in the second region, and
- wherein, of the elastic members, the elastic member located closest to the folding line in the second region is thicker than the elastic member located closest to the free edge in the first region.

* * * * *